(12) United States Patent
Seifert

(10) Patent No.: US 10,631,770 B2
(45) Date of Patent: Apr. 28, 2020

(54) LANCET NEEDLE WITH ALIGNMENT AND RETENTION NOTCH

(71) Applicant: FACET TECHNOLOGIES, LLC, Kennesaw, GA (US)

(72) Inventor: Kevin J. Seifert, Concord, MA (US)

(73) Assignee: FACET TECHNOLOGIES, LLC, Atlanta, GA (US)

( * ) Notice: Subject to any disclaimer, the term of this patent is extended or adjusted under 35 U.S.C. 154(b) by 61 days.

(21) Appl. No.: 14/299,871

(22) Filed: Jun. 9, 2014

(65) Prior Publication Data

US 2014/0364763 A1 Dec. 11, 2014

Related U.S. Application Data

(60) Provisional application No. 61/833,090, filed on Jun. 10, 2013.

(51) Int. Cl.
| | |
|---|---|
| *A61B 5/15* | (2006.01) |
| *B29C 70/68* | (2006.01) |
| *A61B 5/151* | (2006.01) |

(52) U.S. Cl.
CPC .. *A61B 5/150412* (2013.01); *A61B 5/150282* (2013.01); *A61B 5/150435* (2013.01); *A61B 5/150511* (2013.01); *B29C 70/68* (2013.01); *A61B 5/150022* (2013.01); *A61B 5/15151* (2013.01); *A61B 5/15171* (2013.01); *A61B 5/15186* (2013.01)

(58) Field of Classification Search
CPC ........ A61B 5/150412; A61B 5/150435; A61B 5/150511; A61B 5/150519; A61B 5/151; A61B 5/15146; A61B 5/155; A61B 5/150427; A61B 5/150425
See application file for complete search history.

(56) References Cited

U.S. PATENT DOCUMENTS

| | | | | |
|---|---|---|---|---|
| 3,029,815 | A | * 4/1962 | Roehr | A61M 5/343 29/447 |
| 3,093,134 | A | 6/1963 | Roehr | |
| 3,358,689 | A | 12/1967 | Higgins | |
| 3,470,604 | A | * 10/1969 | Zenick | A61M 5/343 264/249 |

(Continued)

FOREIGN PATENT DOCUMENTS

| | | |
|---|---|---|
| EP | 1287785 A1 | 3/2003 |
| WO | 2011158669 A1 | 12/2011 |
| WO | 2013110953 A1 | 8/2013 |

OTHER PUBLICATIONS

International Search Report & Written Opinion of PCT/US2014/041563; dated Aug. 18, 2014; 12 pgs.

*Primary Examiner* — Daniel L Cerioni
*Assistant Examiner* — Yasmeen S Warsi
(74) *Attorney, Agent, or Firm* — Gardner Groff & Greenwald, PC

(57) ABSTRACT

A lancet needle with an alignment and engagement notch, with material of the lancet body extending into the notch to more securely retain the needle to the lancet body, whereby a shorter needle can be utilized than with typical lancets. The notch optionally also provides a registration point for rotational and/or axial alignment of the needle during overmolding to form the lancet body, for example to maintain consistent positioning of the needle's beveled point.

19 Claims, 5 Drawing Sheets

(56) References Cited

U.S. PATENT DOCUMENTS

| | | | |
|---|---|---|---|
| 5,456,875 | A | 10/1995 | Lambert |
| 6,261,272 | B1 | 7/2001 | Gross et al. |
| 6,443,929 | B1 | 9/2002 | Kuracina et al. |
| 6,589,261 | B1 | 7/2003 | Abulhaj et al. |
| 6,629,959 | B2 | 10/2003 | Kuracina et al. |
| 6,723,111 | B2 | 4/2004 | Abulhaj et al. |
| 7,341,573 | B2 | 3/2008 | Ferguson et al. |
| 7,396,334 | B2 * | 7/2008 | Kuhr ............... A61B 5/1411 600/583 |
| 7,655,017 | B2 | 2/2010 | Starnes |
| 8,052,618 | B2 | 11/2011 | Haar et al. |
| 8,075,572 | B2 | 12/2011 | Stefanchik et al. |
| 8,292,873 | B2 | 10/2012 | Mickley et al. |
| 8,377,088 | B2 * | 2/2013 | Nicholls ............ A61B 5/15146 606/181 |
| 8,439,877 | B2 | 5/2013 | Burkholz |
| 8,523,784 | B2 | 9/2013 | Kuhr et al. |
| 2001/0012926 | A1 | 8/2001 | Gross et al. |
| 2004/0092893 | A1 | 5/2004 | Haider et al. |
| 2007/0276425 | A1 * | 11/2007 | Kim ................ A61B 5/150022 606/186 |
| 2008/0243032 | A1 | 10/2008 | Hindelang et al. |
| 2009/0187118 | A1 | 7/2009 | Kim et al. |
| 2009/0209923 | A1 | 8/2009 | Linderoth et al. |
| 2010/0305519 | A1 | 12/2010 | McKinnon et al. |

* cited by examiner

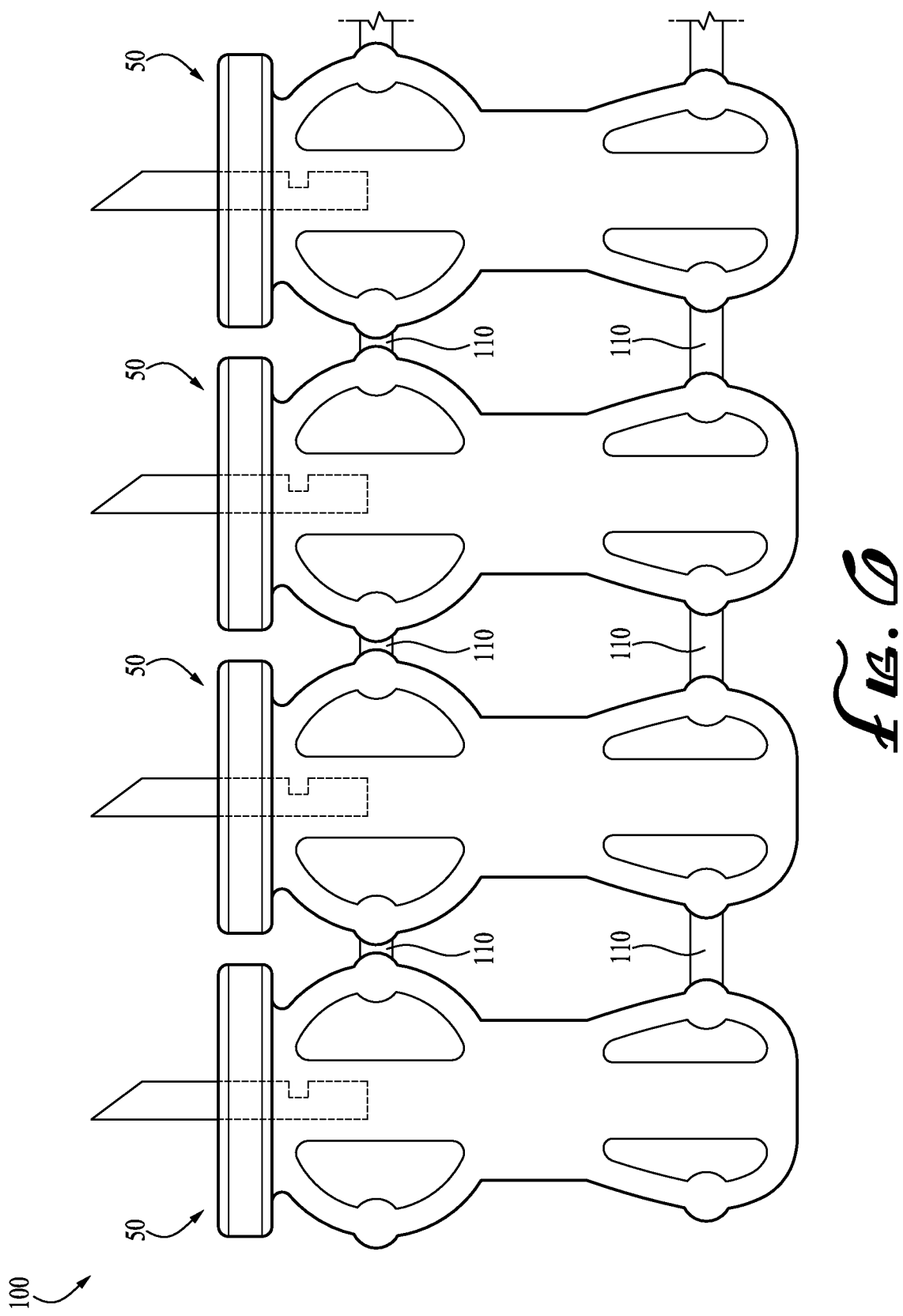

LANCET NEEDLE WITH ALIGNMENT AND RETENTION NOTCH

CROSS-REFERENCE TO RELATED APPLICATION

This application claims the benefit of U.S. Provisional Patent Application Ser. No. 61/833,090 filed Jun. 10, 2013, the entirety of which is hereby incorporated herein by reference for all purposes.

TECHNICAL FIELD

The present invention relates generally to the field of medical devices, and more particularly to lancet needles or cannulas, lancets and lancing devices for blood sampling and testing.

BACKGROUND

Lancets and lancing devices are utilized for penetrating the skin of a human or animal subject at a lancing site to obtain a sample of blood or other body fluid for medical testing, as in blood-typing or blood-glucose testing. Known lancing devices commonly include a housing containing a drive mechanism, a charging mechanism for energizing the spring or other drive means of the drive mechanism, and a release mechanism for releasing the drive mechanism upon actuation. A lancet is typically propelled by the drive mechanism from a retracted position shielded within the housing to an extended position wherein a sharp tip portion of the lancet projects from the housing to prick the subject's skin at a desired lancing site. An ejection mechanism can optionally be included for discharge of a used lancet from the lancing device.

The lancet may be a disposable component that is removably mounted into a receiver or lancet carrier portion of the drive mechanism of a lancing device. A used lancet typically is removed from the lancet carrier after sampling for disposal. A new, sterile lancet is then replaced into the lancet carrier for further sampling. Lancets typically comprise a sharp metal tip in the form of an elongate needle or blade, for example formed of stainless steel. The needle or blade is typically embedded in a plastic body that has a size and shape configured for releasable engagement with the receiver or lancet carrier of a lancing device. The sharp tip of the lancet is commonly embedded in a removable plastic endcap to maintain sterility and prevent inadvertent sticks prior to use. The endcap may be replaceable onto the lancet after use to re-cover the sharp lancet tip for safety and hygienic purposes.

In alternate "single-use" embodiments, the lancet is not intended for removal and replacement, and the entire lancing device and lancet are disposed of after a single use. Single use devices commonly include re-use prevention mechanisms to resist attempts to utilize the device for more than one sampling procedure.

In order to retain the lancet needle securely in place in the lancet body during de-capping, when twisting and pulling forces are commonly imparted on the lancet needle, lancet needles traditionally have a length that corresponds to the length of the plastic lancet body and the distance to which the tip of the lancet needle extends beyond the lancet body, so that the needle has enough contact surface area within the lancet body to resist detachment or loosening of the needle from the plastic body. Also, typical lancet manufacturing processes utilize longitudinally spaced contact points for holding the lancet needle within the mold during molding of the lancet body and maintaining proper axial alignment of the lancet needle. As such, it has until now been considered counterintuitive to those of ordinary skill in the art to seek to significantly reduce the length of the lancet needle within a lancet.

Continuing needs exist for improvements to lancet technology. It is to the provision of improved lancet needles and lancets that the present invention is primarily directed.

SUMMARY

In example embodiments, the present invention provides a notched lancet needle for a lancet, an improved lancet including such a lancet needle, and/or a plurality of such lancets forming a multi-lancet strip or array. Advantageously, the provision of a notch or recess within the side surface of a lancet needle allows for both increased integrity of the engagement of the lancet needle within the lancet body, as well as rotational alignment control of the lancet needle's position relative to the lancet body.

In one aspect, the present invention relates to a lancing needle for a lancet including a generally elongate body, a bevel and a notch. The elongate body extends along a longitudinal axis from a first end to a second end. The bevel or grinding is formed on at least one end of the body to form a sharp lancing tip. The notch is formed on at least a portion of the body between the first end and the second end. Consistent registration is optionally maintained between the rotational positions of the bevel and the notch, such that rotational alignment of the needle tip's sharpening angle relative to the lancet body can be controlled during the molding process.

In another aspect, the invention relates to a lancet including a lancet body and a lancet needle. The lancet body has a first end and a second end, defining a length therebetween. The lancet needle has a needle body including a sharp lancing tip and a notch. The sharp lancing tip projects from the first end of the lancet body. The notch is formed on the needle body and is engaged with a portion of the lancet body between the first and second end thereof. The lancet needle has a length substantially less than the length of the lancet body.

In still another aspect, the invention relates to a multi-lancet strip or array including at least two or more lancets coupled together. Each lancet includes a lancet body and a lancet needle. The lancet body extends from a forward end to a distal end. The lancet needle has a sharp lancing tip extending from the forward end of the lancet body, and a notch spaced a distance from the tip which is embedded within the lancet body. The sharp lancing tip forms a bevel and projects from the first end of the lancet body. The notch is formed on the needle body and is engaged with a portion of the lancet body between the first and second end thereof. Preferably, a consistent registration is maintained between the alignment of the bevel relative to a location of the notch on the needle body among all lancets of the multi-lancet strip.

In another aspect, the invention relates to a method for manufacturing a lancet. The method includes providing a lancet needle having a generally elongate body extending along a longitudinal axis from a first end to a second end, the first end comprising a bevel forming a sharp tip portion, and a notch formed in a portion of the elongate body between the first and second ends, the bevel having a first orientation and the notch having a second orientation relative to the first orientation; aligning the notch of the lancet needle within a mold; and molding a lancet body within the mold and around the lancet needle while maintaining the alignment of the notch within the mold, wherein aligning the notch of the lancet needle within the mold aligns the bevel forming the sharp tip portion relative to the lancet body.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

BRIEF DESCRIPTION OF THE DRAWINGS

FIG. 6 shows a multi-lancet strip or array according to another example embodiment of the present invention.

DETAILED DESCRIPTION OF EXAMPLE EMBODIMENTS

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Figure 1:
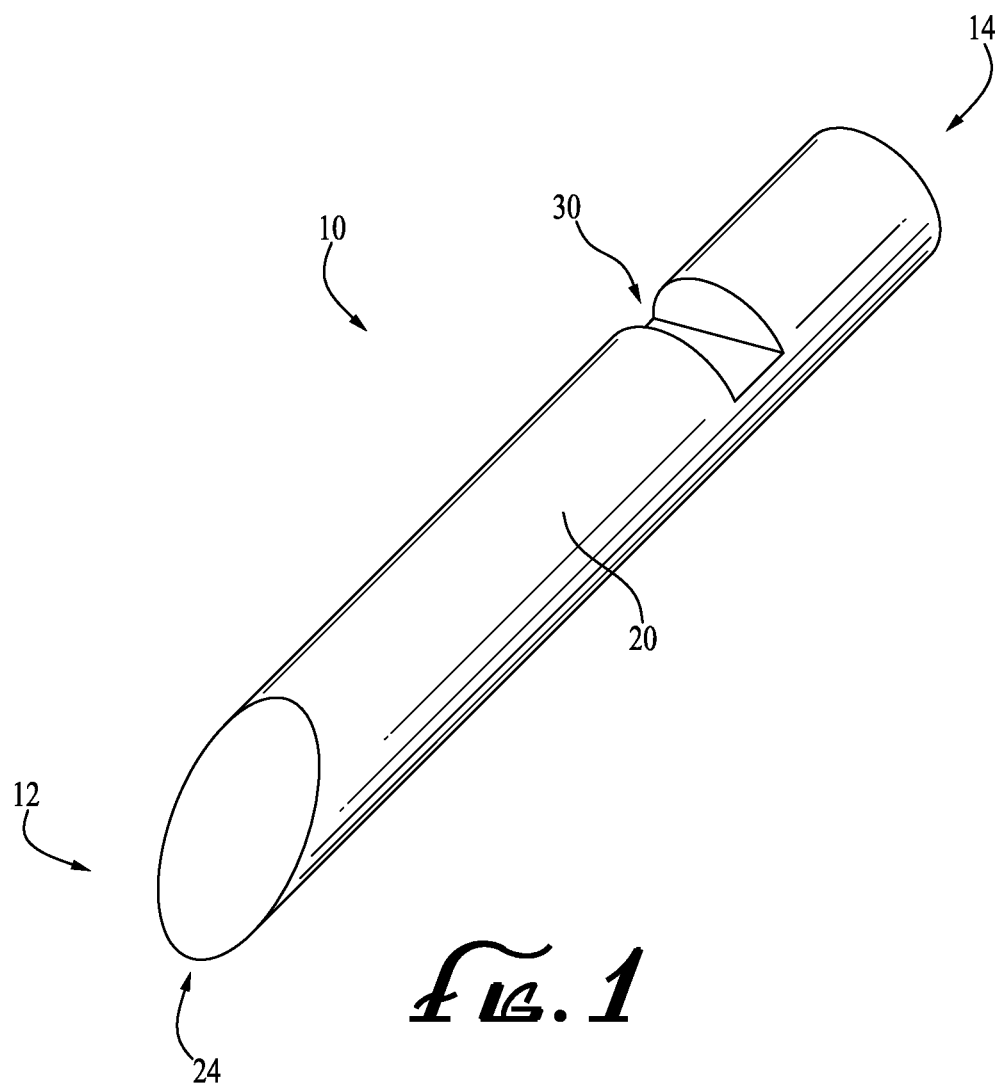
FIG. 1 shows a perspective view of a lancet needle according to an example embodiment of the present invention.
Figure 2:
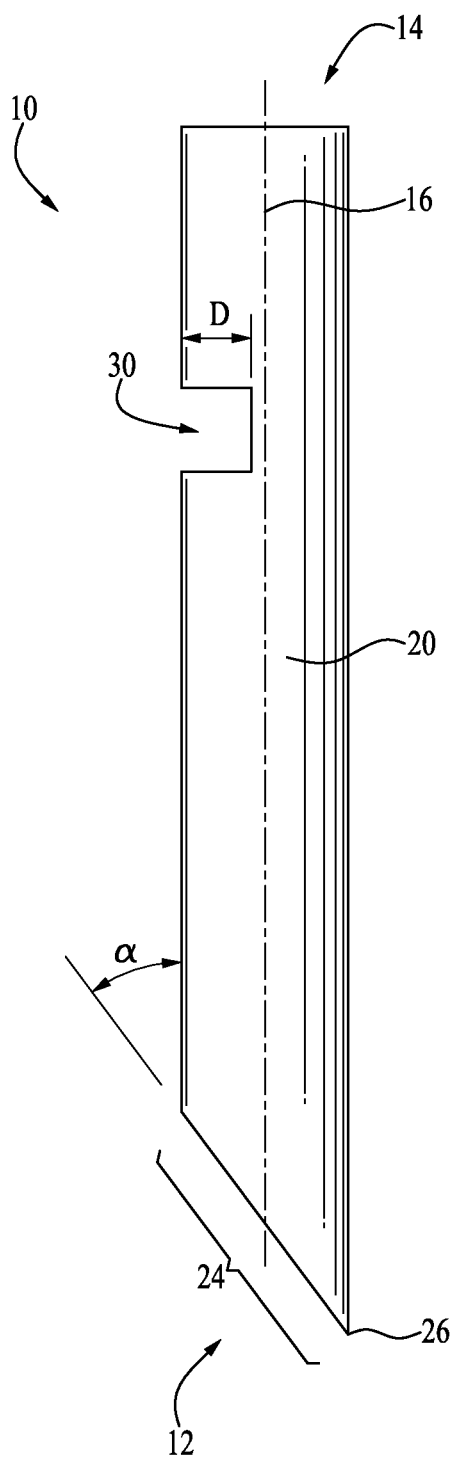
FIG. 2 shows a side view of the lancet needle of FIG. 1.
Figures 3A, 3B:
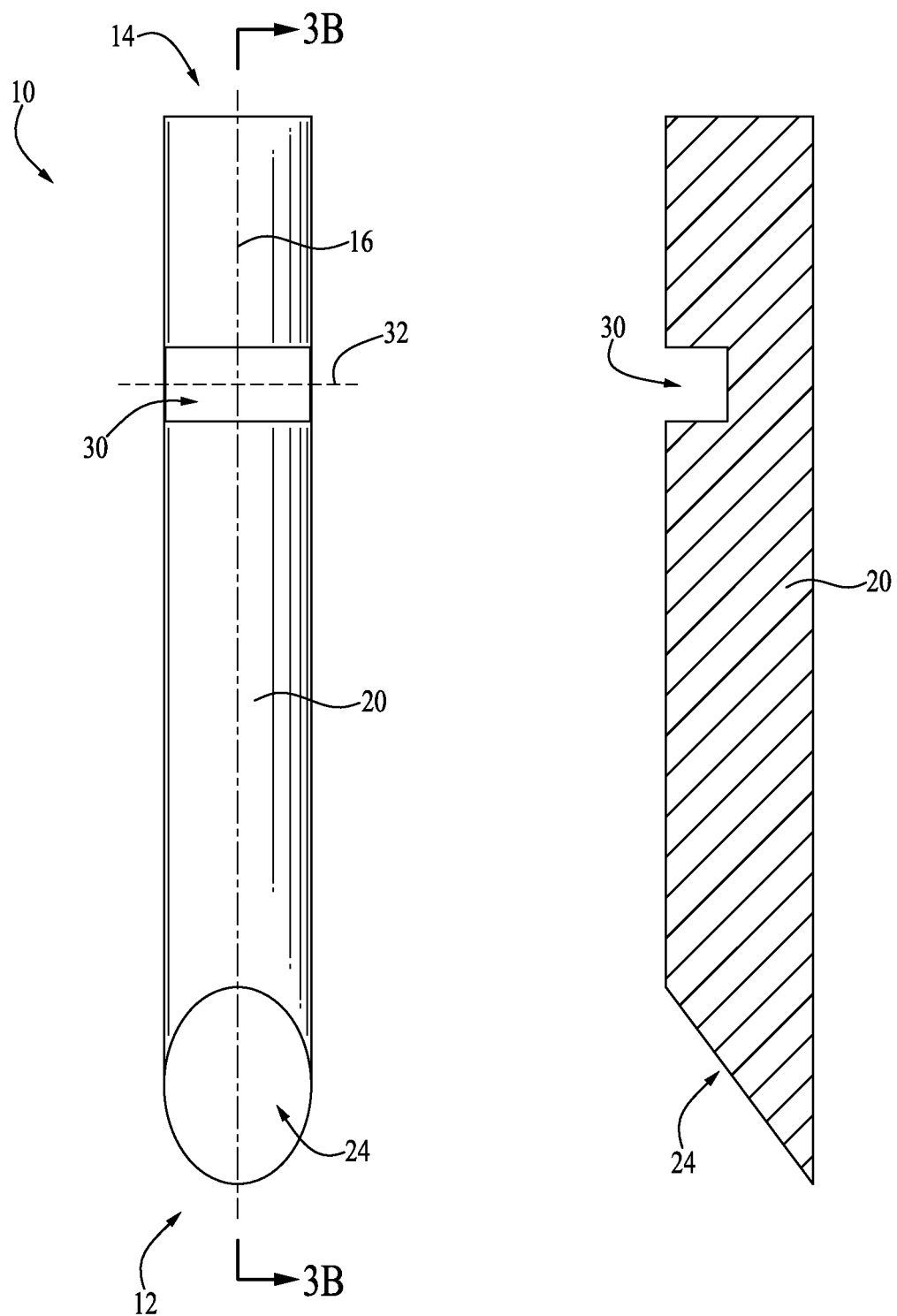
FIG. 3A shows a top view of the lancet needle of FIG. 1.
FIG. 3B shows a cross sectional view of the lancet needle of FIG. 3A taken along line 3A-3A.

With reference now to the drawing figures, wherein like reference numbers represent corresponding parts throughout the several views, FIGS. 1-3 show a lancet cannula or needle 10 according to an example embodiment of the present invention. The lancet needle 10 includes an elongate body 20 extending from a first or proximal end 12 to a second or distal end 14 along a longitudinal axis 16, and defining a lancet needle length between the first and second ends. A bevel or ground point 24 is formed at the first end 12 wherein a sharp lancing tip portion 26 is defined, and a notch or cut-out 30 is formed along a portion of the body 20 between the first and second ends 12, 14, generally proximal the second end.

The bevel 24 formed at the first end 12 defines an angle $\delta$ relative to a side of the body 20, which is generally laterally offset from the longitudinal axis 16 (see FIG. 2). Preferably, the angle $\delta$ is in the range of between about 5-10 degrees, but other angles may be used as desired. Typically, the angle $\delta$ being in the range of between about 5-10 degrees provides that the sharp tip portion 26 is sufficient to penetrate the skin of a human or animal subject with minimal sensation of pain. Optionally, two or more bevels may be formed at the first end 12 in any desired orientation to form a sharp lancing tip.

The notch 30 generally forms a void or indentation within a side surface of the body 20 wherein a notch axis 32 and a notch depth D are defined. In one form, the notch axis 32 is generally transverse to the longitudinal axis 16, and the notch depth D is generally less than about one-half the width or thickness of the body 20. Optionally, the notch axis 32 can be oriented relative to the longitudinal axis 16 as desired, for example, substantially parallel or at an angle relative thereto. The depth D of the notch 30 is also preferably chosen as desired. Optionally, two or more notches may be formed along the body 20 between the first and second ends 12, 14. The cross-sectional geometry of the notch 30 of the depicted embodiment is generally rectangular when viewed from the side (see FIG. 2), but in alternate embodiments may be triangular or V-shaped, rounded or U-shaped, or various other geometries all within the scope of the present invention. The configuration of the notch is optionally matched to cooperative mold tooling used to hold the needle during manufacturing, whereby interengagement of the mold tooling and the notch assists is maintaining alignment of the lancet needle during manufacturing. The notch may be formed by grinding, stamping, embossing, cutting or other fabrication methods. In alternate embodiments, two or more notches may be provided, for example spaced along the length of the needle, and/or offset at different angular positions about the periphery of the needle's sides.

Figure 5:
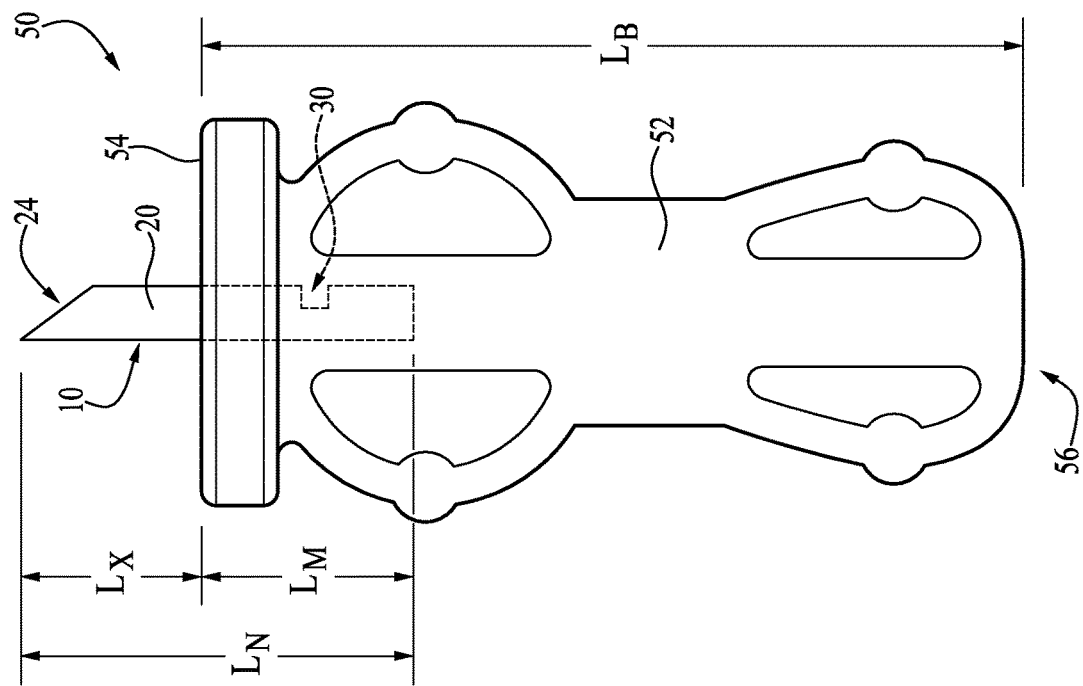
FIG. 5 shows a top view of the lancet of FIG. 4, showing a notch of the needle of FIG. 1 engaged within a body portion of the lancet.
Figure 4:
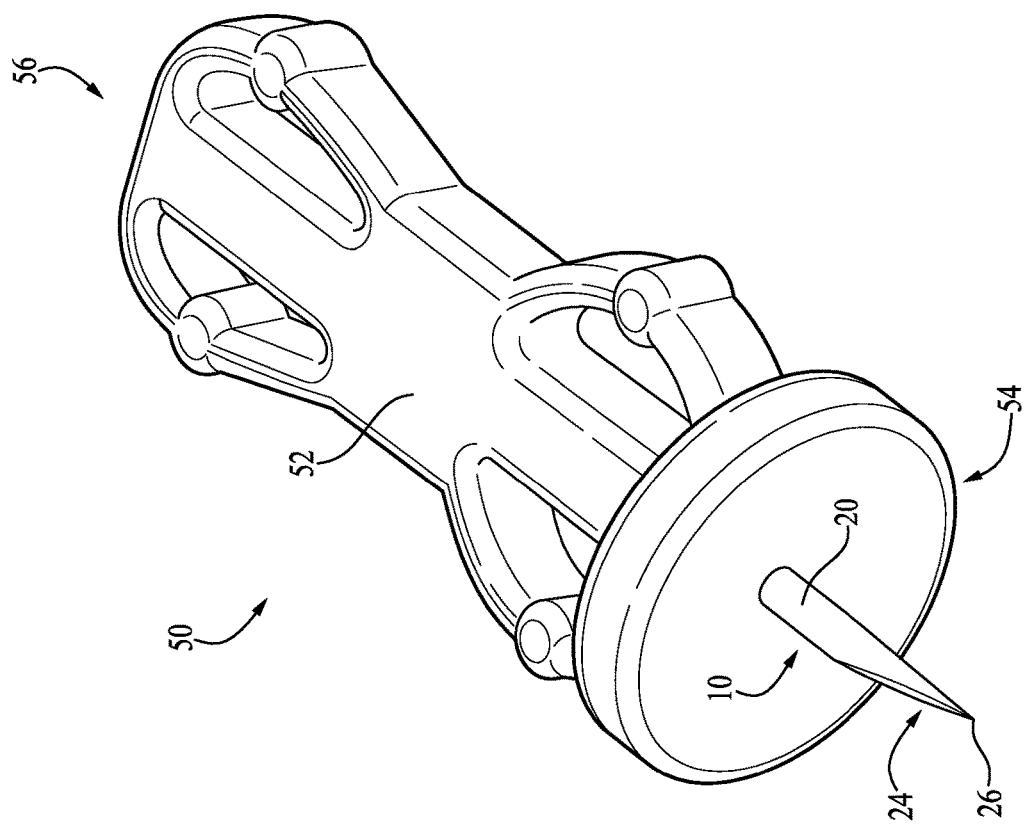
FIG. 4 shows a lancet according to an example embodiment of the present invention, with the needle of FIG. 1 projecting therefrom.

FIGS. 4 and 5 show a lancet 50 including the lancet needle 10 partially embedded within a lancet body 52. Generally, the lancet body 52 defines a length $L_B$, extending between a first end 54 to a second end 56, and has a size and a shape configured for releasable engagement with the receiver or lancet carrier of a corresponding cooperative lancing device. The first end 12 of the needle 10 projects from the first end 54 of the lancet body 52 such that the bevel 24 having the sharp tip portion 26 is exposed. The second end 14 of the needle 10 is embedded within the lancet body 52. Preferably, the notch 30 is engaged with a portion of the lancet body 52 such that the material of the body 52 at least partially fills the void of the notch 30. For example, when manufacturing the lancet 50, the lancet body 52 (generally formed from plastic) is preferably overmolded around the lancet needle 10, which allows the lancet body 52 to substantially engage the lancet needle 10 and fill the void of the notch 30. Thus, with the void at least partially filled during molding, the notch 30 provides adequate surface area for securely mounting the lancet needle 10 to the lancet body 52, thereby providing a better hold between the lancet needle 10 and the lancet body 52. As such, the lancet needle 10 having at least one notch 30 formed thereon preferably reduces the overall length (defined between the first and second ends 12, 14) of the needle 10 that is typically required for manufacturing lancets, thereby reducing material costs.

In example forms, the lancet needle 10 has an overall needle length $L_N$, of which an embedded length $L_M$ portion is embedded within the lancet body 52, and an extended length portion $L_X$ extends beyond the proximal end 54 of the lancet body. In example forms, the needle length $L_N$ is no more than about 75% the length $L_B$ of the lancet body, preferably no more than about 67% the length $L_B$, and still more preferably no more than about 50% the length $L_B$. Otherwise defined, in example embodiments the embedded length $L_M$ of the lancet needle is no more than about 50% the length $L_B$, preferably no more than about 33% the length $L_B$, and still more preferably no more than about 25% the length $L_B$. In further example forms, the retention and alignment notch 30 is positioned approximately midway along the embedded length $L_M$ of the lancet needle (i.e., about $0.5 \times L_B$ from the proximal end 54 of the lancet body).

FIG. 6 shows a multi-lancet strip 100 according to another example embodiment of the present invention. The multi-lancet strip comprises a plurality of lancets 50 removably coupled together to form an array of lancets. The lancets 50 are generally removably coupled together by frangible or separable engagement members 110. Preferably, the engagement members 110 are formed to maintain engagement between the lancets 50 until they are desired to be separated from the array. For example, lancing devices using the multi-lancet strip or cartridge (forming an array of lancets) generally operate in a manner that indexes the strip or cartridge along as the device is being used, and enables tearing or disengaging the engagement members 110 so that a new lancet can be used to prick the subject at a lancing site for each sequential lancing procedure. Optionally, other forms of removably coupling the lancets together may be used as desired.

In example forms, the notch 30 can be used as an identifier or indication feature during manufacture to maintain registration of the needle and align the bevel 24 of each needle 10 relative to the lancet body 52 (see FIGS. 5-6) consistently across all lancets in the array. Preferably, the orientation of the notch 30 relative to the orientation of the bevel 24 is known such that the indication feature (e.g., notch) can be oriented properly within the mold, which ensures that the bevel 24 is properly aligned relative to the lancet body 52. For example, as depicted in FIG. 6, the notch 30 of each needle 10 is similarly aligned (each notch shown on right side of needle) and thereby provides that the bevel 24 of each needle 10 is consistently aligned relative to its respective lancet body 52. Consistent alignment of the bevel in every lancet of the array may permit more consistent positioning and more precise control of the lancing procedure, for example enabling more precise depth control and/or a lower sensation of pain.

The present invention further includes improved methods of manufacturing a lancet. In one form, the method includes providing a lancet needle comprising a generally elongate body extending along a longitudinal axis from a first end to a second end, the first end comprising a bevel forming a sharp tip portion, and a notch formed in a portion of the elongate body between the first and second ends, the bevel having a first orientation and the notch having a second orientation relative to the first orientation; aligning the notch of the lancet needle within a mold; and molding a lancet body within the mold and around the lancet needle while maintaining the alignment of the notch within the mold, wherein aligning the notch of the lancet needle within the mold aligns the bevel forming the sharp tip portion relative to the lancet body. Thus, since the first orientation of the bevel and the second orientation of the notch are known, the notch can be aligned accordingly within the mold to ensure the bevel is properly aligned relative to the lancet body.

While the invention has been described with reference to preferred and example embodiments, it will be understood by those skilled in the art that a variety of modifications, additions and deletions are within the scope of the invention, as defined by the following claims.

What is claimed is:

1. A lancet for a lancing device comprising:
   a lancet body comprising a head portion and a body portion, the head portion positioned at a first end of the lancet body and the body portion extending transversely from the head portion towards a second end of the lancet body opposite the first end,
      wherein the combination of the head and body portions has a length $L_B$, and
      wherein the lancet head portion comprises a generally circular profile and the lancet body portion comprises a generally oblong profile having a first substantially flat side and a second substantially flat side opposite the first side; and
   a lancing needle having a length $L_N$, a portion of the needle being embedded within the head and body portions of the lancet body, the embedded portion having a length $L_M$, the lancing needle comprising:
      an elongate needle body extending along a longitudinal axis;
      a sharp tip formed on an end of the needle body opposite the embedded portion, the sharp tip forming a beveled surface; and
      a notch formed at least partially on the embedded portion;
   wherein the beveled surface is aligned in a predetermined rotational orientation relative to the lancet body and the notch, the notch being oriented substantially perpendicular to the needle body and the flat sides of the lancet body;
   wherein the lancing needle length $L_N$ is no more than 75% the lancing body length $L_B$; and
   wherein the embedded portion length $L_M$ is no more than 50% the lancet body length $L_B$.

2. The lancet of claim 1, wherein the needle body defines a thickness and the notch defines a notch depth of less than one-half the needle body thickness.

3. The lancet of claim 1, wherein the notch defines a notch axis generally transverse to the longitudinal axis of the elongate needle body.

4. The lancet of claim 1, wherein the sharp tip comprises a bevel.

5. The lancet of claim 1, wherein a specified registration is maintained between the notch and the beveled surface.

6. A lancet comprising:
   a lancet needle and a lancet body molded over a portion of the lancet needle;
   wherein the lancet body has a head portion and a body portion, the combination of the head and body portions having a length $L_B$;
   wherein the lancet body further comprises the head portion at a first end of the lancet body and the body portion at a second end of the lancet body, the second end being positioned opposite the first end of the lancet body;
   wherein the lancet head portion comprises a generally circular profile and the lancet body portion comprises a generally oblong profile, the lancet body portion having a first substantially flat side and a second substantially flat side opposite the first side;

wherein the lancet needle having a lancet needle length $L_N$ no more than 75% of the lancet body length $L_B$ comprises an elongate needle body having a sharp lancing tip and a notch, a portion of the needle body being embedded within the lancet body, the embedded portion having a length $L_M$ no more than 50% of the lancet body $L_B$, the notch formed at least partially on the embedded portion of the needle body and engaged with a portion of the lancet body between the first and second end thereof, and the sharp lancing tip projecting from an end of the needle body opposite the embedded portion, and;

wherein the sharp lancing tip comprises a bevel; and wherein the notch is configured for alignment with a cooperative mold tooling, the alignment providing a consistent registration between the bevel, the notch, and the lancet body when the lancet body is molded over the embedded portion of the needle body.

7. The lancet of claim 6, extended length portion $L_X$ of the lancet needle extends beyond the first end of the lancet body.

8. The lancet of claim 6, wherein the overall needle length $L_N$ is no more than 67% the length $L_B$ of the lancet body.

9. The lancet of claim 6, wherein the overall needle length $L_N$ is no more than 50% the length $L_B$ of the lancet body.

10. The lancet of claim 6, wherein the embedded length $L_M$ of the lancet needle is no more than 33% the length $L_B$ of the lancet body.

11. The lancet of claim 6, wherein the notch is positioned midway along an embedded length $L_M$ of the lancet needle.

12. The lancet of claim 6, wherein the lancet needle defines a needle body thickness and the notch defines a notch depth of less than one-half the needle body thickness.

13. The lancet of claim 6, wherein the notch defines a notch axis generally transverse to a longitudinal axis of the lancet needle.

14. The lancet of claim 6, wherein the consistent registration between the lancet body, the notch and the bevel is predetermined.

15. The lancet of claim 1, wherein the beveled surface is aligned obliquely and transverse to the first and second substantially flat surfaces of the lancet body.

16. The lancet of claim 6, wherein the embedded length $L_M$ of the lancet needle is no more than 25% the length $L_B$ of the lancet body.

17. A multi-lancet strip comprising at least two lancets removably coupled together forming an array of lancets, each lancet comprising a lancet body having a length $L_B$ and a lancet needle having a length $L_N$ no more than 75% of the lancet body length $L_B$, the lancet body extending from a first end having a head portion to a second end having a body portion wherein the body portion extends transversely from the head portion towards the second end opposite the first end, the head portion comprising a generally circular profile and the lancet body portion comprising a generally oblong profile with a first substantially flat side and a second substantially flat side opposite the first side, the lancet needle comprising a needle body having a first end and a second end, the needle body having a sharp lancing tip at the first end and a semi-circumferential notch near the second end, the sharp lancing tip forming a bevel and projecting from the first end of the lancet body, the second end of the needle body being embedded within the lancet body wherein the needle body is immovable relative to the lancet body, the embedded portion having a length $L_M$ no more than 50% of the lancet body length $L_B$, and the notch at least partially engaging with a portion of the lancet body between the first and second end thereof, and wherein every lancet of the multi-lancet strip comprises a substantially identical and predefined registration between the bevel, the notch and the lancet body.

18. The multi-lancet strip of claim 17, wherein the notch of each needle is angularly aligned with the bevel.

19. A method for manufacturing a lancet comprising:

providing a lancet needle of length $L_N$ comprising a generally elongate body extending along a longitudinal axis from a first end to a second end, the first end comprising a bevel forming a sharp tip portion, and a notch formed on the elongate body between the first and second ends, the bevel having a first orientation and the notch having a predetermined second orientation relative to the first orientation of the bevel;

aligning the notch of the lancet needle within a mold; and molding a lancet body of length $L_B$ within the mold and around the lancet needle the lancet body comprising a head portion with a generally circular profile at a first end of the lancet body and a body portion with a generally oblong profile at a second end of the lancet body, the body portion extending transversely from the head portion towards the second end of the lancet body opposite the first end, wherein a portion of the lancet needle at its second end is embedded within head and body portions of the lancet body, forming an embedded portion of length $L_M$ no more than 50% of the lancet body length $L_B$, wherein the lancet needle length $L_e$ is no more than 50% of the lancet length $L_e$, wherein the notch of the lancet needle is at least partially embedded in the lancet body, and wherein the notch of the lancet needle is aligned within the mold such that the notch is oriented substantially perpendicular to the needle body and the flat sides of the lancet body aligning the bevel in a predetermined rotational orientation relative to the lancet body.

\* \* \* \* \*